United States Patent
Yokoi et al.

(10) Patent No.: US 8,996,097 B2
(45) Date of Patent: Mar. 31, 2015

(54) OPHTHALMIC MEASURING METHOD AND APPARATUS

(75) Inventors: Norihiko Yokoi, Kyoto (JP); Shigeru Kinoshita, Osaka (JP); Takayoshi Suzuki, Hamamatsu (JP); Yutaka Mizukusa, Chofu (JP); Osamu Yamamoto, Osaka (JP)

(73) Assignees: Norihiko Yokoi (JP); Shigeru Kinoshita (JP); Kowa Company Ltd. (JP)

( * ) Notice: Subject to any disclaimer, the term of this patent is extended or adjusted under 35 U.S.C. 154(b) by 1907 days.

(21) Appl. No.: 11/434,657

(22) Filed: May 15, 2006

(65) Prior Publication Data

US 2006/0263297 A1    Nov. 23, 2006

(30) Foreign Application Priority Data

May 16, 2005    (JP) .................. 2005-142035

(51) Int. Cl.
    *A61B 6/00*      (2006.01)
    *A61B 3/14*      (2006.01)
    (Continued)

(52) U.S. Cl.
    CPC . *A61B 3/101* (2013.01); *A61B 3/10* (2013.01); *A61B 5/0071* (2013.01); *G06T 7/0014* (2013.01); *A61B 3/14* (2013.01);
    (Continued)

(58) Field of Classification Search
    CPC ............... G06T 2207/30041; G06T 7/0014; A61B 5/0071; A61B 3/101; A61B 3/0008; A61B 2576/02; A61B 3/14
    USPC ............... 600/476; 604/294; 351/200, 221
    See application file for complete search history.

(56) References Cited

U.S. PATENT DOCUMENTS 4,747,683 A * 5/1988 Doane .................... 351/206
6,236,459 B1 * 5/2001 Negahdaripour et al. .... 356/496
(Continued)

FOREIGN PATENT DOCUMENTS

| DE | 3108878 | 9/1982 |
| EP | 1029504 | 8/2000 |
| JP | 2000237135 | 9/2000 |

OTHER PUBLICATIONS

Eiki Goto and Scheffer C.G. Tseng:, "Kinetic Analysis of Tear Interference Images in Aqueous Tear Deficiency Dry Eye before and after Punctal Occlusion", Investigative & Visual Science, vol. 44, No. 5, May 1, 2003, pp. 1897-1905, XP002391239.

*Primary Examiner* — Long V Le
*Assistant Examiner* — Helene Bor
(74) *Attorney, Agent, or Firm* — Adams & Wilks

(57) ABSTRACT

In an ophthalmic measuring method, a traceable marker in particulate form is administered to the lachrymal fluid of a subject's eye, and the lachrymal fluid is irradiated with illuminating light. Images of the illuminated lachrymal fluid are electronically captured respectively at different times. Two images from among the captured images are selected, with each of the two selected images displaying the traceable marker. A characteristic point of each of the two selected images is specified. A movement speed of the traceable marker is measured based on positions thereof in the two selected images and on a time difference from specifying the characteristic point of one of the two selected images to specifying the characteristic point of the other of the two selected images. The measured movement speed of the traceable marker is outputted as the movement speed of the lachrymal fluid of the subject's eye.

7 Claims, 4 Drawing Sheets

(51) Int. Cl.
  *A61B 1/04* (2006.01)
  *A61B 3/10* (2006.01)
  *A61B 5/00* (2006.01)
  *G06T 7/00* (2006.01)
(52) U.S. Cl.
  CPC .............. *A61M2210/0612* (2013.01); *G06T 2207/30041* (2013.01); *A61B 2576/02* (2013.01)

USPC .............................. 600/476; 351/206; 348/78

(56) References Cited

U.S. PATENT DOCUMENTS

| | | | |
|---|---|---|---|
| 6,299,305 B1 * | 10/2001 | Miwa | 351/200 |
| 2002/0180929 A1 | 12/2002 | Tseng et al. | 351/206 |
| 2005/0159657 A1 * | 7/2005 | Cappo et al. | 600/315 |

* cited by examiner

OPHTHALMIC MEASURING METHOD AND APPARATUS

CROSS-REFERENCE TO RELATED APPLICATIONS

This application claims priority from Japanese Application No. 2005-142035 filed May 16, 2005, which is hereby incorporated by reference herein.

BACKGROUND OF THE INVENTION

1. Field of the Invention

The present invention relates to an ophthalmic measuring method and apparatus that can be used to screen dry eye and evaluate dry eye severity in a subject's eye.

2. Description of the Prior Art

The recent increase in the number of patients with dry eye is considered to be caused by an increased number of workers at VDTs (Visual Display Terminal), contact lens wearers or the dryness of air-conditioned rooms. Disorders in the corneal epithelium, conjunctival epithelium, and various other ophthalmic disorders can occur in conjunction with dry eye, and the diagnosis of dry eye has become an important subject of ophthalmic field.

Configurations have been proposed in the past for an ophthalmic apparatus for capturing an image of the lachrymal fluid layer of a subject's eye and observing, analyzing, and measuring the image in order to quantitatively evaluate conditions of dry eye.

Embodiments of known techniques include a technique (see Japanese Laid-open Patent Application Publication No. 1997-201334) for capturing an image of an interference pattern formed in the lachrymal fluid surface layer of a subject's eye, and evaluating dry eye conditions based on the hue of a plurality of areas in the image of the interference pattern; and a technique (see Japanese Laid-open Patent Application Publication No. 1999-267102) for projecting an image of an aperture having a prescribed shape onto the surface of lachrymal fluid accumulated in the lachrymal fluid meniscus along the lower eyelid, capturing an image of the aperture projected on the lachrymal fluid surface, finding the curvature radius of the lachrymal fluid surface from the magnification factor of the aperture image, and evaluating dry eye severity.

In the conventional techniques, particularly the technique described in Japanese Laid-open Patent Application Publication No. 1997-201334, an image of the interference color of the lachrymal fluid layer is captured, and the image is observed, analyzed, and measured, but almost no interference color occurs in the normal eye and the eye experiencing the worst severity of dry eye, and this conventional technique suffers from drawbacks in that the normal eye or the eye experiencing the worst severity of dry eye cannot be observed, analyzed, and measured.

In view of the foregoing drawbacks, an object of the present invention is to ensure that the movement speed of lachrymal fluid can be reliably measured, diagnosis can be quantitatively performed from the movement speed of the lachrymal fluid thus measured even on a severely dry eye, and the state of a normal eye can be reliably identified.

SUMMARY OF THE INVENTION

The present invention provides an ophthalmic measuring method comprising the steps of administering a target substance to the lachrymal fluid of a subject's eye; irradiating the lachrymal fluid with illuminating light; electronically capturing a plurality of images of the illuminated lachrymal fluid of the subject's eye, the images being captured respectively at different times; measuring the movement speed of the target substance based on the positions thereof in the images selected among the plurality of captured images and the capturing times of the selected images; and outputting the measured movement speed of the target substance as the movement speed of the lachrymal fluid of the subject's eye.

The present invention also provides an ophthalmic measuring apparatus comprising means for electronically capturing an image of the lachrymal fluid layer in a prescribed position of a subject's eye to which a target substance is administered; means for selecting images among a plurality of images captured; means for computing the movement speed of the target substance based on the positions thereof in the selected images and the capturing times of the selected images; and means for outputting the computed movement speed of the target substance as the movement speed of the lachrymal fluid of the subject's eye.

According to the present invention, an image of the lachrymal fluid layer in a specific position of the subject's eye to which a target substance is administered is electronically captured a plurality of times, the image signal captured each time is computed and comparatively analyzed, and the movement speed of the target substance is measured as the movement speed of the lachrymal fluid of the subject's eye. The severity of dry eye is thus quantitatively evaluated based on the results of measuring the movement speed of the lachrymal fluid of the subject's eye.

In the present invention, a target substance is administered to the subject's eye and its movement in the lachrymal fluid can be monitored even when an interference color does not occur. Therefore, the movement speed of lachrymal fluid can be quantified regardless of the state of the subject's eye, and there is no occurrence of the drawback of the prior art in which it was difficult to distinguish between a normal eye and a severely dry eye.

DESCRIPTION OF THE PREFERRED EMBODIMENTS

Embodiments of the present invention will be described hereinafter with reference to the drawings.

Figure 1:
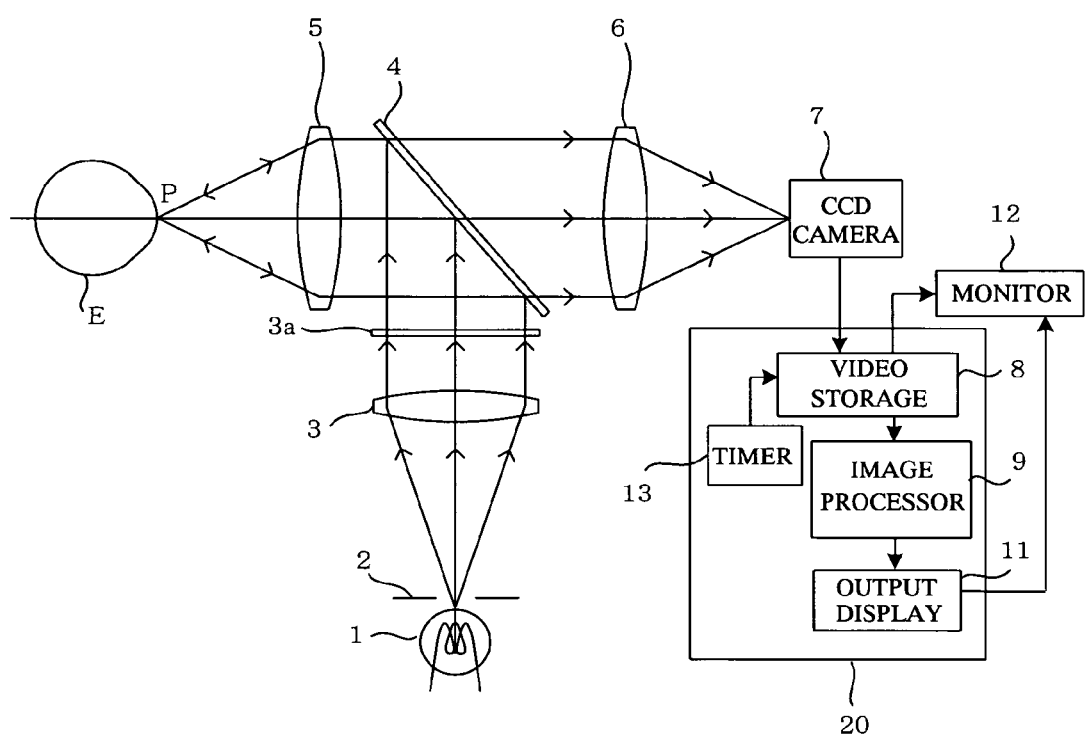
FIG. 1 is a block diagram showing one embodiment of an ophthalmic measuring apparatus according to the present invention.

FIG. 1 shows the simplified structure of an ophthalmic measuring apparatus according to the present invention. In this drawing, the reference numeral 1 indicates a white light source composed of a halogen lamp or the like for illuminating a subject's eye E. Light radiated from the white light source 1 passes through a mask 2 for limiting the field of illumination, and then illuminates a prescribed point P on the subject's eye E via a lens 3, an exciter filter 3a, a half mirror 4, and a lens 5. The position selected for this prescribed point P is the lipid layer of the outermost lachrymal fluid layer on the cornea of the subject's eye E. The intensity of the white light source 1 can be adjusted by a dimmer circuit (not shown in the drawing).

The light reflected from point P enters a color CCD camera 7 via the lens 5, the half mirror 4, and a lens 6, and the RGB (color) video signal thus captured is inputted to an image processing device 20.

The image processing device 20 can be configured so as to utilize a personal computer (PC) or other hardware. This image processing device 20 has a video storage device 8 that is composed of a video capture interface and an HDD or other external storage device and is capable of real-time image output and the like to a monitor 12; an image processor 9 composed of a CPU and memory (ROM and RAM) or other computing resources; an output display controller 11 that uses the monitor 12 and controls the output display described hereinafter; and a timer 13 used for controlling the image acquisition timing of the video storage device 8, the timing of image output to the monitor 12, and other timings.

The image processing device 20 also has a keyboard, a pointing device (mouse or the like), or another common operating device not shown in the drawings. The monitor 12 is used as described hereinafter for output displays relating to ophthalmic measurement, and the abovementioned operating device and monitor 12 constitute a user interface for ophthalmic measurement.

The operation according to the configuration described above will next be described.

In the present embodiment, a target substance (tracer, marker, or other particulate substance, colorant, or the like that is not harmful to the test subject/subject's eye) is directly or indirectly administered to the lachrymal fluid of the subject's eye, the illuminating light of the white light source 1 is radiated, an image of the lachrymal fluid of the subject's eye is electronically captured two or more times at different times by the CCD camera 7, each image signal thus captured is computed and comparatively analyzed, and the movement speed of the target substance is measured as the movement speed of the lachrymal fluid of the subject's eye. The severity of dry eye can be quantitatively evaluated based on these results of measuring the movement speed of the lachrymal fluid of the subject's eye.

The target substance is administered to the subject's eye by administering the subject's eye with an eye drop or ointment that includes the target substance, or by using another method. When a fluorescent target substance is used, the exciter filter 3a is inserted in the optical path, and a barrier filter (not shown) is inserted in the optical path along the CCD camera 7.

Figure 2:
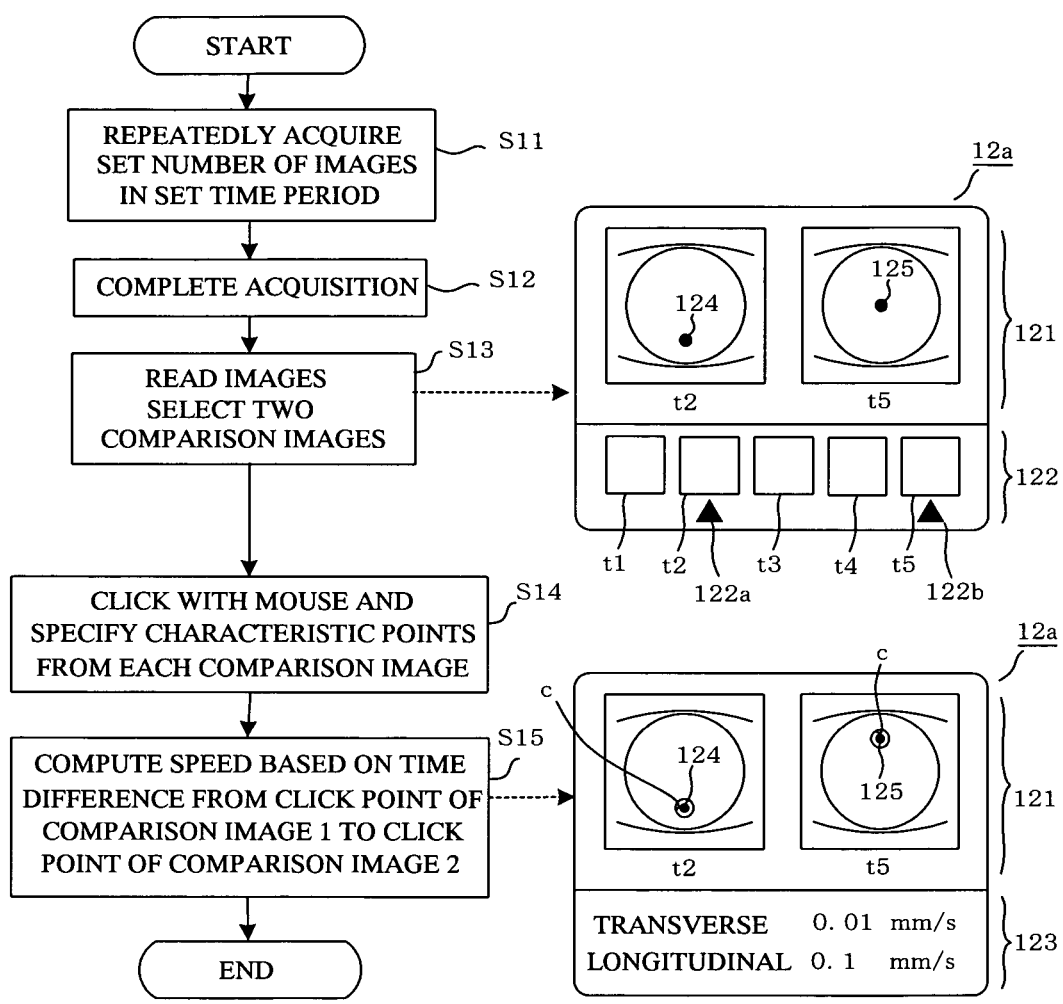
FIG. 2 is a diagram showing the operation in the configuration shown in FIG. 1.

After the target substance is administered to the subject's eye, measurement is performed according to the control sequence shown in FIG. 2. FIG. 2 shows the control sequence in the configuration of FIG. 1, and the state of the output display on the monitor 12. The control sequence of FIG. 2 is stored in advance in the ROM (or HDD or the like) storage device of the image processor 9 shown in FIG. 1.

After the target substance is administered to the subject's eye, and blinking is confirmed in the subject's eye, the user performs a prescribed operation (using a keyboard or other device not shown in the drawing) to initiate imaging. In step S11 of FIG. 2, the illuminating light of the white light source 1 is directed to the subject's eye, and an image of the illuminated location is received by the video storage device 8 of the CCD camera 7.

An imaging period of about six seconds, for embodiment, is set at this time, and about 10 to 100 images are automatically and continuously captured. When 100 images are captured in six seconds, the image capture interval is 0.06 seconds. The appropriate imaging period is considered to be at least several seconds, since it is preferred that the target movement speed be able to be measured after blinking of the subject's eye following administration of the target substance. The timer 13 is used to control the capture timing described above, and the capture time data of each image are stored in the video storage device 8 after being correlated with the captured images.

After image acquisition is completed in step S12, in step S13, the image processor 9 controls the monitor 12 via the output display controller 11 and creates an output display such as the one shown in the upper right of FIG. 2. In this arrangement, the screen 12a of the monitor 12 is divided into top and bottom portions, the top portion is the main display area 121, the bottom portion is the thumbnail display area 122, and a plurality of size-reduced thumbnail images of the captured images are displayed in the thumbnail display area 122.

In the thumbnail display area 122, cursors 122a and 122b are displayed, and two images used for measuring the lachrymal fluid movement speed can be selected by matching these cursors 122a and 122b with the bottom of a thumbnail in the thumbnail display area 122 using a keyboard or pointing device (mouse or the like) not shown in the drawing and performing a prescribed selection operation.

In the embodiment depicted in the drawing, a state is shown in which images t2 and t5 are selected among five thumbnail images t1 through t5, and images t2 and t5 (comparison images) corresponding to these thumbnail images t2 and t5 are displayed in the main display area 121.

Target substances 124 and 125 are displayed in the images t2 and t5, respectively, in the main display area 121. It is apparent that since the same target substance must be used to measure the movement speed of the lachrymal fluid, the user is required to select two images that show target substances 124 and 125 which are considered to be the same.

When the user can determine that target substances 124 and 125 are displayed that are considered to be the same, then in step S14, the user specifies the images of the target substances 124 and 125 by clicking them using the pointing device (mouse or the like) as indicated by the reference symbol C in the lower right of FIG. 2.

Thus, in step S15, the lachrymal fluid movement speed is computed based on the distance between the target substances 124 and 125 considered to be the same in the two comparison images t2 and t5, and on the elapsed time found from the imaging time data of the comparison images t2 and t5. In order for a prescribed image magnification to be obtained in this distance computation, the measuring apparatus shown in FIG. 1 is aligned in advance with the subject's eye so that the actual distance is reliably obtained from the distance in the image, or a device capable of stereo imaging is used as the CCD camera 7 so that the actual distance is obtained from the distance in the image.

According to the operation described above, the movement speed of lachrymal fluid can be computed, and the results thereof can be displayed as shown in the lower right of FIG. 2. The bottom portion of the screen 12a in this arrangement is changed to a measurement results area 123, and the lachrymal fluid movement speed in the transverse direction and lachrymal fluid movement speed in the longitudinal direction are numerically displayed in the measurement results area 123.

According to the present embodiment as described above, the target substance is administered to the lachrymal fluid of the subject's eye, the illuminating light of the white light source 1 is radiated, an image of the lachrymal fluid of the subject's eye is electronically captured two or more times at different times by the CCD camera 7, the lachrymal fluid movement speed found from the images thus obtained can be displayed, and based on these results, the user can evaluate the severity of dry eye.

Since the target substance is administered to the lachrymal fluid of the subject's eye and imaged according to the present embodiment, the movement of the lachrymal fluid can be monitored even when an interference color does not occur, the movement speed of lachrymal fluid can be quantified regardless of the state of the subject's eye, and it is possible to overcome the drawback of the conventional configuration in which it was difficult to distinguish between a normal eye and a severely dry eye.

In the embodiment above the target substance was administered to the lachrymal fluid of the subject's eye, and the surface of the lachrymal fluid on the cornea of the subject's eye was imaged, but it is also possible to adopt a configuration in which the layer of lachrymal fluid accumulated in the lachrymal fluid meniscus along the lower eyelid of the subject's eye is imaged, as in the following embodiment.

Figure 3:
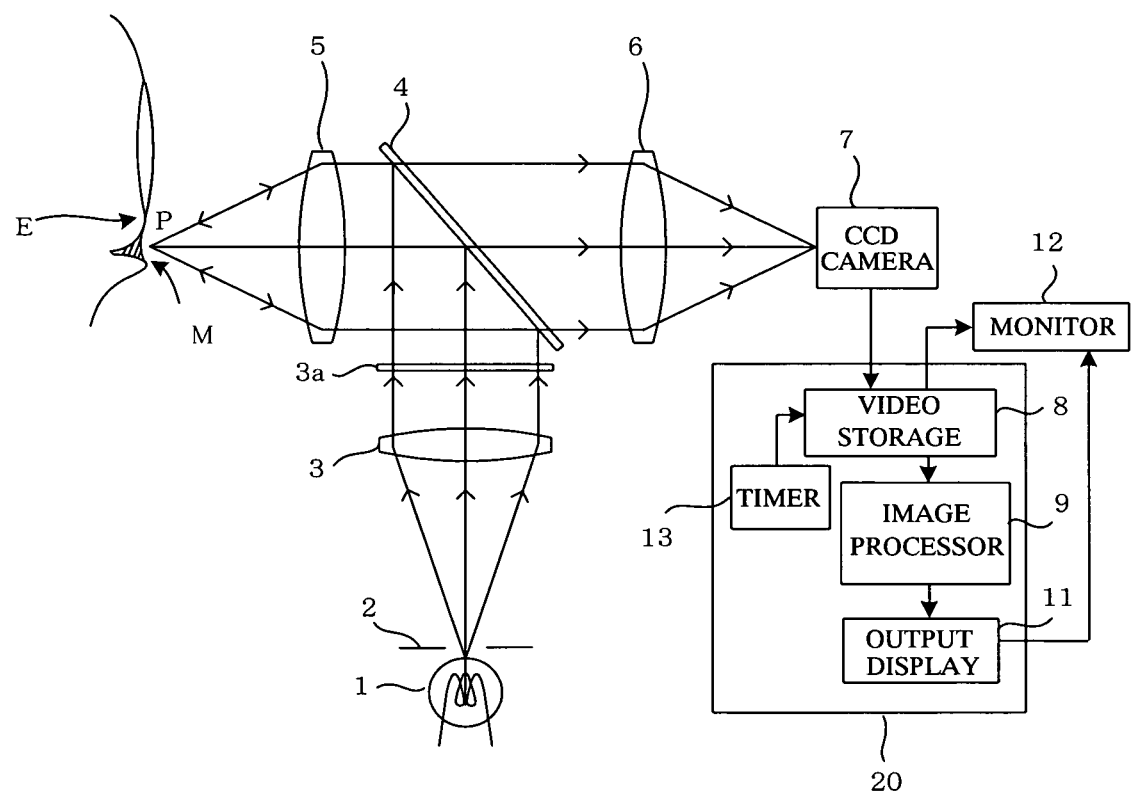
FIG. 3 is a block diagram showing another embodiment of an ophthalmic measuring apparatus according to the present invention.

FIG. 3 depicts the manner in which measurement is performed in this embodiment. The hardware of the measuring apparatus in FIG. 3 is the same as in FIG. 1, but the illumination and optical axis of imaging by the measuring apparatus are aligned so that imaging is performed in the location of the lachrymal fluid layer (lachrymal fluid meniscus) accumulated in the lachrymal fluid meniscus along the lower eyelid of the subject's eye. The lachrymal fluid moves along the edge of the lower eyelid when the subject's eye blinks.

In this type of configuration as well, the target substance is administered to the lachrymal fluid of the subject's eye, and the severity of dry eye can be evaluated from the movement speed of the target substance that is moving in the lachrymal fluid meniscus on the edge of the lower eyelid of the subject's eye.

The overall sequence of the measurement operation in the present embodiment is substantially the same as in the previously described embodiment, except that the illumination and optical axis of imaging by the measuring apparatus are aligned in the vicinity of the lachrymal fluid meniscus along the lower eyelid of the subject's eye.

Figure 4:
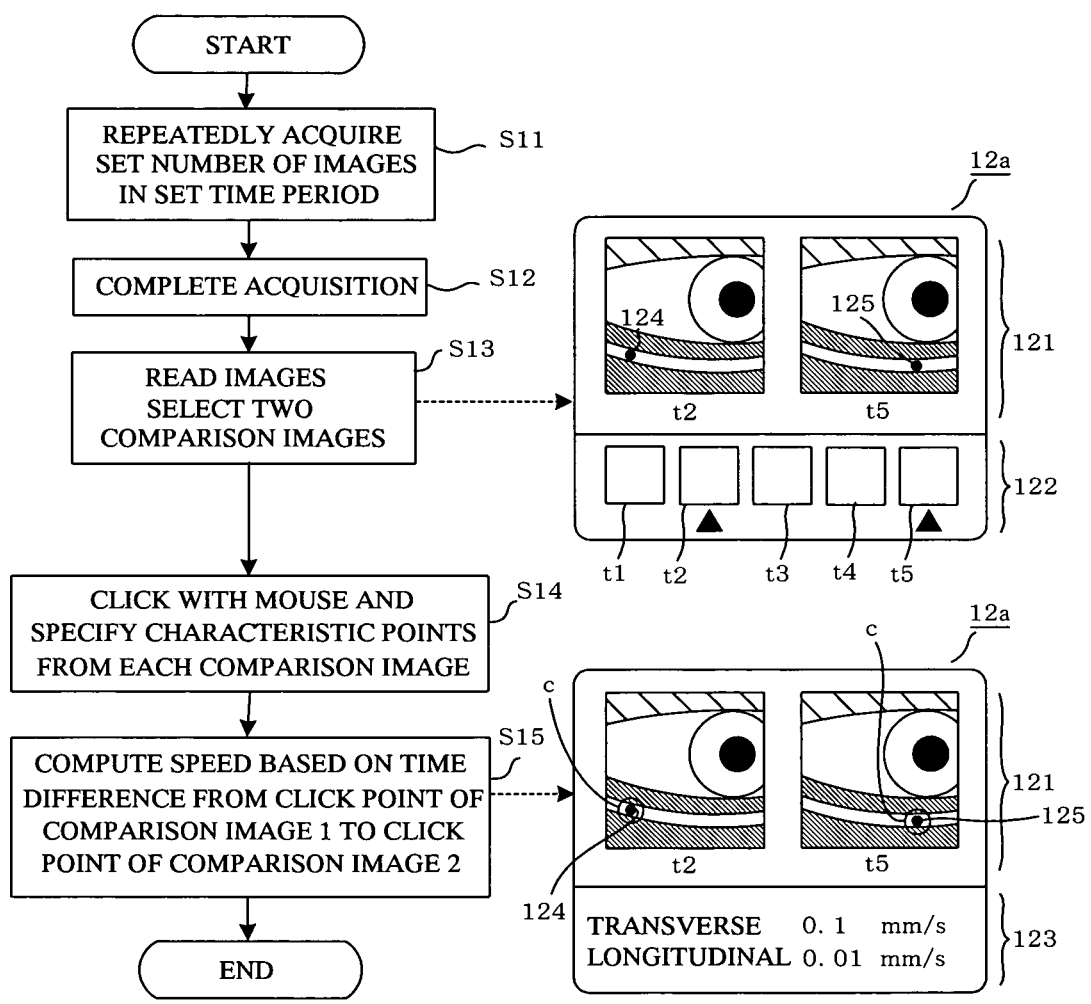
FIG. 4 is a diagram showing the operation in the configuration shown in FIG. 3.

FIG. 4 shows the manner in which measurement control and output display are performed in the present embodiment, and uses the same format as FIG. 2. The flowchart portion on the left side of FIG. 4 is the same as in FIG. 2, and the format of the output display on the right side of FIG. 4 is the same as in FIG. 2.

In the same manner as in the previously described embodiment, the target substance is administered to the subject's eye by administering the subject's eye with an eye drop or ointment that includes the target substance, and after the target substance is administered to the subject's eye, measurement is performed according to the control sequence shown in FIG. 4.

After the target substance is administered to the subject's eye, and blinking is confirmed in the subject's eye, the user performs a prescribed operation (using a keyboard or other device not shown in the drawing) to initiate imaging. A prescribed number of images are then captured within the prescribed imaging period in steps S11 and S12. The imaging interval and number of images captured are the same as in the previously described embodiment.

In step S13, the comparison images (t2 and t5) are displayed in the main display area 121 when two comparison images (t2 and t5) are selected using the thumbnail display area 122 of the screen 12a of the monitor 12 in the same manner as in the previously described embodiment.

At this time, the user selects the two images that show target substances 124 and 125 which are considered to be the same.

When the images of the target substances 124 and 125 are specified by being clicked on with the pointing device (mouse or the like) as indicated by the reference symbol C in step S14, the computation routine of step S15 is executed, and the lachrymal fluid movement speed is computed based on the distance between the target substances 124 and 125 considered to be the same in the two comparison images t2 and t5, and on the elapsed time found from the imaging time data of the comparison images t2 and t5.

According to the operation described above, the lachrymal fluid movement speed can be computed, and the results can be displayed as shown in the lower right of FIG. 4.

According to the present embodiment as described above, the target substance is administered to the lachrymal fluid of the subject's eye, the illuminating light of the white light source 1 is radiated, an image of the lachrymal fluid meniscus of the subject's eye is captured two or more times at different times by the CCD camera 7, the lachrymal fluid movement speed found from the images thus obtained can be displayed, and based on these results, the user can evaluate the severity of dry eye.

Since the target substance is administered to the lachrymal fluid of the subject's eye and is imaged according to the present embodiment, the movement of the lachrymal fluid can be monitored even when an interference color does not occur, the movement speed of lachrymal fluid can be quantified regardless of the state of the subject's eye, and it is possible to overcome the drawback of the conventional configuration in which it was difficult to distinguish between a normal eye and a severely dry eye.

The ophthalmic measuring apparatus of the present invention includes many components in its hardware that are shared by common configurations of ophthalmic imaging devices, and can therefore be implemented easily and at low cost using an existing ophthalmic imaging device. The ophthalmic measuring method of the present invention can also be easily and inexpensively implemented in the same manner in existing ophthalmic imaging hardware, or in partially modified hardware.

What is claimed is:

1. An ophthalmic measuring method comprising the steps of:
   administering to the lachrymal fluid of a subject's eye a traceable marker that is in particulate form on the lachrymal fluid;
   irradiating with illuminating light the lachrymal fluid to which the traceable marker has been administered;
   electronically capturing a plurality of images of the illuminated lachrymal fluid of the subject's eye, the images being captured respectively at different times;
   selecting two images from among the plurality of captured images, each of the two selected images displaying the traceable marker;
   specifying a characteristic point of each of the two selected images;
   measuring a movement speed of the traceable marker based on positions thereof in the two selected images and on a time difference from specifying the characteristic point of one of the two selected images to specifying the characteristic point of the other of the two selected images; and outputting the measured movement speed of the traceable marker as the movement speed of the lachrymal fluid of the subject's eye.

2. An ophthalmic measuring method according to claim 1; wherein the traceable marker is included in an eye drop or ointment that is administered to the subject's eye.

3. An ophthalmic measuring method according to claim 1; wherein the images are captured at the lachrymal fluid layer on the corneal surface of the subject's eye to which the traceable marker has been administered, or at the position of the lachrymal fluid layer accumulated in the lachrymal fluid meniscus of the subject's eye.

4. An ophthalmic measuring apparatus comprising:
means for electronically capturing a plurality of images of the lachrymal fluid layer in a prescribed position of a subject's eye to which a traceable marker that is in particulate form is administered;
means for selecting two images from among the plurality of captured images, each of the two selected images displaying the traceable marker;
means for specifying a characteristic point of each of the two selected images;
means for computing a movement speed of the traceable marker based on positions thereof in the two selected images and on a time difference from specifying the characteristic point of one of the two selected images to specifying the characteristic point of the other of the two selected images; and
means for outputting the computed movement speed of the traceable marker as the movement speed of the lachrymal fluid in the lachrymal fluid layer of the subject's eye.

5. An ophthalmic measuring apparatus according to claim 4; wherein the images are captured at the lachrymal fluid layer on the corneal surface of the subject's eye to which the traceable marker has been administered, or at the position of the lachrymal fluid layer accumulated in the lachrymal fluid meniscus of the subject's eye.

6. An ophthalmic measuring apparatus comprising:
means for irradiating with illuminating light the lachrymal fluid of a subject's eye to which a traceable marker in particulate form has been administered;
means for electronically capturing a plurality of images of the illuminated lachrymal fluid of the subject's eye, the images displaying the traceable marker and being captured respectively at different times;
means for selecting two images from the plurality of captured images;
means for specifying a characteristic point of each of the two selected images displaying the traceable marker;
means for measuring a movement speed of the traceable marker based on the positions thereof in the two selected images and on a time difference from specifying the characteristic point of one of the two selected images to specifying the characteristic point of the other of the two selected images; and
means for outputting the measured movement speed of the traceable marker as the movement speed of the lachrymal fluid of the subject's eye.

7. An ophthalmic measuring apparatus according to claim 6; wherein the means for electronically capturing captures the images at the lachrymal fluid layer on the corneal surface of the subject's eye to which the traceable marker has been administered, or at the position of the lachrymal fluid layer accumulated in the lachrymal fluid meniscus of the subject's eye.

* * * * *